United States Patent [19]

Wegner

[11] Patent Number: 5,078,900

[45] Date of Patent: Jan. 7, 1992

[54] PROCESS FOR REMOVING DISSOLVED CONTAMINANTS FROM AQUEOUS SOLUTIONS USING GETTERS AND REVERSIBLY DISPERSIBLE CARRIERS

[75] Inventor: Paul C. Wegner, San Carlos, Calif.

[73] Assignee: Tiegel Manufacturing Co., Belmont, Calif.

[21] Appl. No.: 389,378

[22] Filed: Aug. 4, 1989

[51] Int. Cl.$^5$ .............................................. C02F 1/54
[52] U.S. Cl. ................................. 210/728; 210/638; 210/729; 210/908; 210/909; 210/912
[58] Field of Search ............... 210/634, 638, 643, 725, 210/727, 728, 729, 912, 908, 909

[56] References Cited

U.S. PATENT DOCUMENTS

| | | | |
|---|---|---|---|
| 3,158,570 | 11/1964 | Duke | 210/912 |
| 3,203,968 | 8/1965 | Scbba | 210/904 |
| 3,238,127 | 3/1966 | Sebba | 210/704 |
| 3,586,477 | 6/1971 | Flood | 210/638 |
| 3,755,158 | 8/1973 | Tnazuka et al. | 210/725 |
| 4,226,791 | 10/1980 | Reinhardt | 210/638 |
| 4,631,132 | 12/1986 | Jones | 210/727 |
| 4,681,958 | 7/1987 | Halbert et al. | 556/42 |
| 4,731,187 | 3/1988 | Moriya et al. | 210/725 |

FOREIGN PATENT DOCUMENTS

| | | | |
|---|---|---|---|
| 53-4358 | 1/1978 | Japan | 210/912 |
| 56-7683 | 1/1981 | Japan | 210/727 |

Primary Examiner—Peter Hruskoci
Attorney, Agent, or Firm—Frank J. Benasutti

[57] ABSTRACT

A process for purifying contaminated aqueous solutions without using ion exchange resins or organic solvents is provided. The process comprises contacting an aqueous solution with a getter compound and a non-polymeric carrier compound in a dispersed state to remove dissolved contaminants or recover dissolved valuable materials. Suitable carrier compounds having pendant long chain hydrocarbon radicals and hydrophilic moieties are disclosed. The process is highly efficient and effective for removing a wide variety of dissolved contaminants such as metal ions, non-metal ions and dissolved organic contaminants such as dyes.

7 Claims, No Drawings

PROCESS FOR REMOVING DISSOLVED CONTAMINANTS FROM AQUEOUS SOLUTIONS USING GETTERS AND REVERSIBLY DISPERSIBLE CARRIERS

FIELD OF THE INVENTION

The present invention relates to a process for removing contaminants or recovering valuable materials from aqueous solutions. More particularly, it relates to the efficient and effective removal of dissolved contaminants such as toxic metal ions from wastewater by utilizing getters and reversibly dispersible carriers.

BACKGROUND OF THE INVENTION

A significant problem in the chemical industry is the treatment of wastewater and other process streams to remove pollutants to environmentally acceptable levels. Millions of gallons of wastewater contaminated with heavy metals and other pollutants are generated each day which must be treated to reduce the amount of pollutants to very low levels. For example, particularly toxic pollutants such as lead and mercury must be reduced to 50 ppb and 2 ppb, respectively. The following Table I sets forth a list of "priority" pollutants established under the Clean Water Act and the current federal drinking water and maximum allowable river discharge limits.

TABLE I

| EPA Priority Pollutant Elements | Maximum Allowable Concentrations (ppm) |
| --- | --- |
| Antimony | 0.15 |
| Arsenic | 0.05 |
| Beryllium | 0.000037 |
| Cadmium | 0.01 |
| Chromium | 0.05 |
| Copper | 1.0 |
| Lead | 0.05 |
| Mercury | 0.002 |
| Nickel | 0.013 |
| Selenium | 0.01 |
| Silver | 0.05 |
| Thallium | 0.013 |
| Zinc | 5.0 |

The need to remove pollutants from large volumes to wastewater to these very low levels has pushed currently available technologies to their limits. Aside from the ability to achieve low levels of contamination, a number of other features are desired in a process for treating wastewater. It is important to be able to treat polluted water in a cost effective manner. In addition to cost effective operation of the process, it is desirable to minimize any required changes to existing water pollution equipment. It is also desirable to reduce the size of a treatment plant as much as possible by increasing the processing rate. In some cases, it is desirable to use a recyclable material to remove the pollutants, so long as the regeneration process does not create more pollution than it eliminates. A wastewater treatment process should create as little solid waste as possible. Finally, the process should not create additional pollution problems such as polluting the treated water with other environmental pollutants.

One of the most popular technologies for treating wastewater is based on a settling process using lime. Calcium hydroxide or magnesium hydroxide is added to the water in a settling tank to absorb the offending contaminant. This technology permits the processing of large volumes without adding polluting chemicals and uses very simple equipment. However, in many cases, the contaminant concentration cannot be reduced low enough to meet EPA standards without using excessive amounts of material and long processing times. Additionally, large amounts of solid hazardous waste in the form of sludge are produced which cannot be effectively regenerated. While landfill has been the most popular means of disposing of sludge, it is rapidly becoming an unacceptable method of handling hazardous waste. Thus, using this technology, the contaminated wastewater problem is essentially being replaced by a solid hazardous waste disposal problem.

Another popular method of cleaning contaminated wastewater is the use of ion exchange resins to filter out the contaminants. Generally speaking, the advantages of ion exchange resins are that it is regenerable, it does not pollute the treated water and usually no separation process is required to remove the ion exchange resin from the treated water. However, the use of ion exchange resins to treat wastewater has a number of disadvantages.

Ion exchange resin processes are slow, very expensive and have low efficiencies. In order to be effective, the wastewater must be passed through a significant amount of resin, usually in the form of a filter bed. This is acceptable for treating small volumes of water to achieve certain levels of purity (e.g., 0.1 ppm of lead). However, as the desired level of purity (e.g. 0.05 ppm of lead) and volume of water increase, this technology becomes increasingly slow or less effective. The complex fabrication process and sophisticated synthetic chemistry involved in developing and producing ion exchange resins significantly contributes to the expense of using ion exchange resins to purify liquid waste and limits the variety of resins available. Ion exchange resin beds may be regenerated, but the wastewater from the regeneration must be treated to remove bulk toxins and then usually passed through the ion exchange resin again to eliminate all the polluted water.

Another technology for removing water soluble material is solvent extraction. This technology is not used in the waste water treatment industry, but rather for reclaiming materials of value such as in the mining industry. In solvent extraction processes, an organic solvent such as kerosene is contacted with the water containing the material to be reclaimed. The organic solvent contains an extractant compound which is preferably highly soluble in the organic phase and significantly less soluble in the aqueous phase. The extractant compound complexes with the material to be removed and the complexed extractant-material remains dissolved in the solvent. The organic and aqueous phases are then separated such as by decanting. The primary advantages of solvent extraction are speed, effectiveness, and ease of regeneration. The extractant compounds are also generally easier to synthesize than ion exchange resins. Therefore, a much broader variety of materials is commercially available and extractants may be tailored to selectively extract particular materials. However, solvent extraction does have disadvantages that make this technology unsuitable for the purification of wastewater.

One major disadvantage is that solvent extraction leaves solvent and extractant residues in the processed water thus creating another pollution problem. The solvents and in some cases the extractants are environmentally toxic. The solvents are generally flammable and toxic which creates an environmental hazard. They may also be expensive thereby contributing to the expense of the process. If regeneration cannot be used, it takes a large volume of solvent to treat a given volume of water and solvent extraction may be prohibitively expensive. While the solvents are easier to regenerate than ion exchange resin and yield a much smaller volume of regeneration waste, the wastes still must be treated, creating yet another pollution problem.

The process of the present invention has the advantages of the above technologies with few disadvantages and is also highly efficient and effective for purifying aqueous solutions. The same equipment that is commonly found in most large scale water and municipal water treatment plants (i.e., settling process equipment) may be used to practice the present process. For a given volume of wastewater, the processing time is generally much less than for ion exchange resins or settling and comparable with processing time for solvent extractions. However, unlike solvent extraction, potentially toxic and flammable solvents are not introduced into the water. Compared to lime settling treatment, very little sludge is produced, yet low contaminant concentrations that meet EPA regulations may be achieved. The getters and carriers used in the present process may be regenerated easily with inexpensive chemicals without producing excessive regeneration wastewater. Because relatively small amounts of sludge are generated and the getters and carriers are not usually expensive compounds, the wastes may optionally be disposed of by landfill or incineration.

SUMMARY OF THE INVENTION

The present invention provides a process for removing a dissolved contaminant from an aqueous solution comprising: contacting the aqueous solution with a getter and a non-polymeric, reversibly dispersible carrier in a dispersed state to form a getter-contaminant material; removing the getter-contaminant material by reducing the dispersibility of the carrier to form a discontinuous phase containing the getter-contaminant material and separating the discontinuous phase from the aqueous solution.

A process for purifying contaminated aqueous solutions without using ion exchange resins or organic solvents is provided. The process comprises contacting an aqueous solution with a getter compound and a non-polymeric carrier compound in a dispersed state to remove dissolved contaminants or recover dissolved valuable materials. Suitable carriers having pendant long chain hydrocarbon radicals and hydrophilic moieties are disclosed. The process is highly efficient and effective for removing a wide variety of dissolved contaminants such as metal ions, non-metal ions and dissolved organic contaminants such as dyes.

DETAILED DESCRIPTION OF THE INVENTION

According to the process of the present invention, a getter and a reversibly dispersible carrier are contacted with a contaminated aqueous solution in a dispersed state. The getter and dissolved contaminant form a getter-contaminant material which is believed to be in the form of a complex. The getter-contaminant material is then removed by reducing the dispersibility of the carrier in the aqueous solution to form a discontinuous, preferably solid, phase which may be separated from the aqueous solution.

The process of the present invention is useful to remove a wide variety of dissolved contaminants such as aluminum, antimony, arsenic, beryllium, boron, cadmium, cesium, chromimum, cobalt, copper, iron, lead, mercury, nickel, plutonium, selenium, silver, thallium, uranium, vanadium, zinc, and the like and dissolved organic contaminants such as polychlorinated biphenyls (PCBs), trichloroethylene, DDT, fluoroscene, trihalomethanes, trihalomethane precursors, dyestuffs such as methylene blue and the like. The process may also be used to recover dissolved valuable metal, non-metal and organic ions.

A "reversibly dispersible carrier" is a non-polymeric compound which is substantially insoluble in water having at least one pendant hydrophobic moiety and at least one hydrophilic moiety. The pendant hydrophobic moiety is preferably a long chain ($C_{14}$–$C_{32}$, more preferably $C_{18}$–$C_{32}$) n-alkyl group and most preferably a stearyl group. When more than one pendant hydrophobic moiety is present, the total number of carbon atoms on these moieties should be preferably 16 or greater. Thus, two pendant $C_{10}$ straight chain hydrocarbon radicals will generally impart sufficient hydrophobicity. Suitable carriers include, for example, stearic acid, stearyl phosphate, distearyl phosphate, stearyl amine, the like and mixtures thereof.

A suitable carrier must be sufficiently water insoluble so that excessive amounts of the carrier compound do not dissolve in the aqueous solution. However, the carrier must also be dispersible on an essentially molecular level in water so that it may be placed in a dispersed state. It has been found that while polymers having complexing moieties such as ion exchange resins are highly water insoluble, they are not readily dispersible because of their high molecular weight. In contrast, the carrier compounds used in the present process are both substantially water insoluble and dispersible. These carriers are generally not useful in solvent extraction, because they have poor solubility ($<2\%$) in typical hydrocarbon solvents.

While not being bound by any particular theory, it is believed that the pendant long chain hydrocarbon radicals such as stearyl radicals impart high water insolubility to the carriers while permitting the carriers to be highly dispersed in water. Thus, these carrier compounds are dispersible on an essentially molecular level. The carrier may be analogized as having a "soap-like tail" covalently bonded directly to the hydrophilic moiety or to a linking group which is bonded to a hydrophilic moiety. It is believed that the hydrophobic moiety of the carrier molecule has an affinity for the hydrophobic moiety of the getter molecule which causes the getter to be dispersed and coagulated with the carrier in the present process.

A "getter" is a non-polymeric, substantially water insoluble compound having at least one pendant hydrophobic moiety and at least one ion complexing moiety. The complexing moiety is preferably an ion having an affinity for the contaminant ion desired to be removed from the aqueous solution. The pendant hydrophobic moiety may be a substituted or unsubstituted alkyl, cycloalkyl, alkoxyalkyl, alkycycloalkyl, aryl, alkylaryl, aralkyl and cycloalkylaryl, preferably unsubstituted branched or straight chain alkyl, radical having 1-32 carbon atoms. Generally, extractants known in solvent extraction processes may be used as getters in the process of the present invention.

Suitable getters include, for example, dithiophosphinates such as bis (2,4,4-trimethylpentyl) dithiophosphinate, diisobutyldithiophosphinate, di-2-ethylhexyl dithiophosphinate; phosphates such as di-2-ethylhexyl phosphate, tributyl phosphate; dithiophosphates such a dicyclohexyl dithiophosphate; amines; sulfides; sulfonates; carbamates; dithiocarbamates such as bis-dimethyl-thiocarbamoyl monosulfide, bis-diethyl-thiocarbamoyl disulfide, bis-pentamethylene-thiocarbamoyl tetrasulfide, bis-dimethyl-thiocarbamoyl disulfide; the like and mixtures thereof.

Table II below summarizes the efficiency, effectiveness, and speed that the various technologies have in treating the same volume of water.

$K_g$ is a measure of the relative efficiency of various processing materials. It assumes a linear relation between the amount of material used and the amount of metal taken out. The larger the $K_g$ is, the more water a given amount of getter can treat and still remove the contaminant to a certain level.

$$K_g = \frac{[\text{Weight of metal removed}]}{[\text{Weight of material used}] \times [\text{Weight of metal remaining}]} \times 100,000$$

A large $K_g$ indicates high efficiency. Getters and carriers which impart a $K_g$ of 20,000 or greater to the process of the present invention are preferred.

$K_{gs}$ is a measure of the relative amount of water that can be processed in the same amount of time assuming a given $K_g$ efficiency:

$$K_{gs} = K_g/\text{process time in minutes}$$

A large $K_{gs}$ indicates fast and efficient processes. Processes having a $K_g$ of 20,000 and a $K_{gs}$ of 500 or greater are preferred in the present invention.

preferred to prepare a stock dispersion which is subsequently mixed into the aqueous solution with agitation.

Because of its high surface area in the dispersed state, the getter readily complexes with the contaminant. The amount of getter used in the process will depend upon factors such as the concentration of the contaminant in the aqueous solution, the desired reduction in contaminant concentration sought, and volume of the aqueous solution being treated. However, it is generally preferred to use an excess of the desired molar reduction of contaminant.

The molar ratio of getter to carrier may vary of from about 10:1 to about 1:10 and will depend upon the dispersibility of the getter. Larger amounts of carrier will be necessary if the getter has poor dispersibility or the getter has extremely high dispersibility (which would inhibit coagulation).

After the contaminated aqueous solution has been contacted with a getter and carrier in dispersed state to form a getter-contaminant material, typically a getter-contaminant complex, the getter-contaminant material may be removed. In contrast to solvent extraction where the getter-contaminant is isolated in a continuous organic solvent phase, the present process comprises forming a discontinuous, usually solid, phase of coalesced particles by simply reducing the dispersibility of carrier. The dispersibility is reduced by reducing the ionizability of the hydrophilic moiety or "polar head" of the carrier by the introduction of an activator or other means of activating by pushing the ionized versus unionized equilibrium towards the unionized state. An activator may be selected with reference to the solubility product ($K_{sp}$) of the carrier in association with the activator. One advantage of this mechanism and process is that the carrier associated with getter-contaminant material and residual carrier are both made less dispersible. While not wishing to be limited, five basic tech-

TABLE II

| | | RELATIVE PERFORMANCE OF VARIOUS TREATMENTS FOR PROCESSING ONE LITER OF WATER | | | | | |
|---|---|---|---|---|---|---|---|
| MATL TYPE | TYPE OF REAGENT | AMOUNT OF MATERIAL REAGENT USED | WEIGHT OF METAL IN WATER | | TREATMENT TIME | RELATIVE EFFICIENCY $K_g$ | RELATIVE SPEED EQUAL EFFICIENCY $K_{gs}$ |
| | | | INITIAL | FINAL | | | |
| Pb | Ion Exchange DP-1+ | 1,000 mg | 50 mg | 0.05 mg | 660 min | 9,100 | 14 |
| Dye | Ion Exchange DP-1+ | 20,000 mg | 2 mg | 0.20 mg | 1 min | 5 | 5 |
| Pb | Magnesium Hydroxide | 1,000 mg | 10 mg | 0.05 mg | 100 min | 20,000 | 200 |
| Cd | Solvent Extraction* | 401,000 mg | 36 mg | 1.6 mg | 3 min | 5.6 | 1.9 |
| Pb | Example° | 150 mg | 10 mg | .005 mg | 30 min | 1,300,000 | 44,000 |

+Amberlite DP-1 ion exchange resin available from Rohm and Haas Company, Philadelphia, Pennsylvania.
*Includes weight of solvent.
°Includes weight of salt, carrier and getter used in process.

In the present process, a getter compound must be placed in a dispersed state. This ma be achieved by dispersing the getter with a carrier compound directly in the contaminated aqueous solution or by predispersing the getter and carrier in a stock aqueous dispersion which is subsequently contacted with the contaminated aqueous solution. A stock dispersion may be prepared using known dispersing techniques such as using dispersing agents, heating water (preferably above the kraft point of the carrier) or adjusting the pH of the water. The particular method of placing the getter and carrier in a dispersed state will largely depend upon the pH, temperature, and ion composition of the contaminated aqueous solution. For example, in treating an acidic contaminated aqueous solution, it is generally niques will be discussed:

(1) Adjusting the pH of the aqueous solution. This will depend largely upon the particular carrier used in the process. For example, stearyl phosphate may be made less dispersible by the addition of an acid such as nitric acid and stearyl amine may be made less dispersible by the addition of sodium hydroxide.

(2) Adding divalent or polyvalent metal ions to the aqueous solution. For example, stearyl phosphate may be made less dispersible by the addition of magnesium sulfate to the aqueous solution.

(3) Forming a non-ionizable (water insoluble) salt in the aqueous solution. In the case of stearyl phosphate, this may be achieved by the addition of silver nitrate.

rial is then allowed to settle and/or is filtered from the aqueous solution.

TABLE III

| Metal/Toxin | Initial In ppm | Final In ppb | Getter w/Carrier Getter Carrier | Amount In grams | Activator | Amount In grams |
|---|---|---|---|---|---|---|
| Lead | 10 | 18 | Cyanex 301* Stearyl phosphate | .05 .05 | Ferric Sulfate | 0.1 |
| Lead | 10 | 1,800 | Cyanex 301 Stearyl phosphate | .05 .05 | Sulfuric Acid | 0.1 |
| Lead | 10 | <5 | Cyanex 301 Stearyl phosphate | .05 .05 | Magnesium Sulfate | 0.1 |
| Lead | 10 | <5 | Cyanex 301 Stearyl phosphate | .025 .025 | Magnesium Sulfate | 0.1 |
| Copper | 10 | 510 | Cyanex 301 Stearyl phosphate | .05 .05 | Magnesium Sulfate | 0.1 |
| Copper | 10 | 610 | Cyanex 301 Stearyl phosphate | .05 .05 | Ferric sulfate | 0.1 |
| Copper | 10 | 310 | Cyanex 301 Stearyl phosphate | .05 .05 | Sodium sulfate | 1.0 |
| Copper | 10 | <0.5 | Cyanex 301 Stearyl phosphate | .05 .05 | Sulfuric Acid | 0.1 |
| Lead | .3 | <0.5 | Cyanex 301 Sodium Stearate | .1 .1 | Magnesium Sulfate | N/A |

*Cyanex 301 is bis (2,4,4-trimethylpentyl) dithiophosphinic acid available from American Cyanamid Company, Wayne, New Jersey.

(4) Adding a salt to reduce dispersibility by the common ion effect. Thus sodium sulfate, potassium sulfate or sodium phosphate may be added to reduce the dispersibility of stearyl phosphate.

(5) Changing the temperature of the aqueous solution. Generally, lowering the temperature decreases dispersibility.

Where an acid, salt or base is added to the aqueous solution to reduce the dispersibility of the carrier, it has been found that the effectiveness of the process may also be affected. Therefore, it is desirable to use acids, salts or bases which are "non-competitive" with the getter-contaminant complex, i.e., do not compete with the contaminant ion to complex with the getter. It is preferred that the added acid, salt or base tends to promote the complexing of the ionized contaminant with residual uncomplexed getter.

In some instances, the addition of an acid, salt or base to reduce dispersibility will not be necessary, since the contaminated aqueous solution may contain, in addition to the contaminant, an acid, salt or base which tends to reduce the dispersibility of the carrier. In treating such contaminated aqueous solutions, it is desirable to first prepare a stock aqueous dispersion of the getter and carrier which is subsequently mixed with the contaminated solution.

The getter-contaminant material in the discontinuous phase may be separated from the aqueous solution using known techniques such as filtering, flocking and/or settling. The getter and carrier may be regenerated using techniques generally known for regenerating contaminant loaded extractants in solvent extraction processing.

The examples set forth in Table III below are illustrative of the process of the present invention. In the examples, the following general procedure was used to treat 1 liter of contaminated aqueous solution. Getter or getter salt and carrier are predispersed in water, usually hot water. It is then added to the contaminated water and is stirred for 15-30 minutes. The activator for reducing dispersibility and about 1 mg of flocking agent are then added together to the aqueous solution and stirred for an additional 30 minutes. The getter-contaminant mate-

I claim:

1. A process for removing a dissolved contaminant from an aqueous solution comprising:
    contacting said aqueous solution with a getter compound selected from the group consisting of bis(2,4,4-trimethylpentyl) dithiophosphinate, diisobutyl dithiophosphinate, di-2-ethyl hexyl dithiophosphinate, di-2-ethylhexyl phosphate, tributy phosphate, bis-diethylthiocarbamoyl disulfide, and bis-dimethyl-thiocarbamoyl disulfide and a nonpolymeric, substantially water-insoluble, reversibly dispersible, soap-like carrier compound having at least one pendant hydrophobic moiety and at least one hydrophilic moiety in a dispersed state to form a getter-contaminant material;
    removing said getter-contaminant material by reducing the dispersibility of said carrier compound to form a discontinuous phase containing said getter-contaminant material and separating said discontinuous phase from said aqueous solution.

2. A process according to claim 1, wherein the carrier compound has at least one covalently bonded pendant n-alkyl radical of 18 to 32 carbon atoms.

3. A process according to claim 1, wherein the carrier compound has at least one covalently bonded pendant stearyl radical.

4. A process according to claim 1, wherein the carrier compound is selected from the group consisting of stearic acid, stearyl phosphate, stearyl amine and mixtures thereof.

5. A process according to claim 1, wherein the getter compound is placed in a dispersed state by dispersing the getter and carrier compound in a stock aqueous dispersion.

6. A process according to claim 5, wherein the getter compound is contacted with the aqueous solution by mixing the stock aqueous dispersion with the aqueous solution.

7. A process according to claim 6, wherein the carrier compound is selected from the group consisting of stearyl phosphate, stearyl amine and stearic acid.

* * * * *